United States Patent [19]

Wiegers et al.

[11] Patent Number: 4,604,232
[45] Date of Patent: Aug. 5, 1986

[54] METHYL-SUBSTITUTED CYCLOHEXENYL ACETALDEHYDES, ORGANOLEPTIC USES THEREOF, PROCESSES FOR PRODUCING SAME AND INTERMEDIATES USEFUL THEREIN

[75] Inventors: Wilhelmus J. Wiegers, Red Bank; Manfred H. Vock, Locust, both of N.J.

[73] Assignee: International Flavors & Fragrances Inc., New York, N.Y.

[21] Appl. No.: 712,170

[22] Filed: Mar. 15, 1985

[51] Int. Cl.⁴ .................................... C11B 9/00
[52] U.S. Cl. ........................ 252/522 R; 568/444; 568/446
[58] Field of Search .................... 568/446, 444; 252/522 R

[56] References Cited

U.S. PATENT DOCUMENTS

| | | | |
|---|---|---|---|
| 4,026,824 | 5/1977 | Pitted et al. | 252/522 R |
| 4,036,774 | 7/1977 | Ovwerkerki et al. | 252/522 R |
| 4,416,902 | 11/1983 | Moorkherjee et al. | 568/446 |
| 4,424,379 | 1/1984 | Sprecker et al. | 568/446 |

OTHER PUBLICATIONS

Duraisamy et al., "J. Amer. Chem. Soc.", vol. 105, pp. 3252-3269 (1983).

Primary Examiner—Werren B. Lone
Attorney, Agent, or Firm—Arthur L. Liberman

[57] ABSTRACT

Described are the compounds defined according to the generic structure:

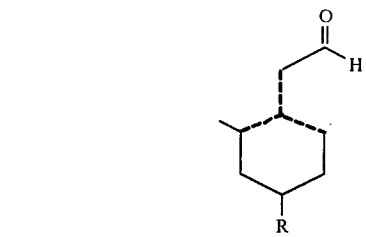

wherein R represents hydrogen or methyl and one of the dashed lines represents a carbon-carbon double bond and each of the other of the dashed lines represent carbon-carbon single bonds. Also described are mixtures of methyl-substituted cyclohexenyl acetaldehydes defined according to the structure:

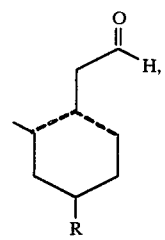

a sub-genus of the genus having the structure:

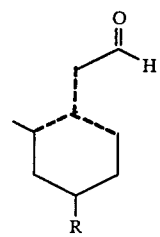

wherein one of the dashed lines represents a carbon-carbon double bond and the other of the dashed lines represents a carbon-carbon single bond and R represents hydrogen or methyl, and uses thereof in augmenting or enhancing the aroma or taste of consumable materials, including perfume compositions, colognes, perfumed articles, perfumed polymers, foodstuffs, chewing gums, medicinal products and toothpastes.

3 Claims, 8 Drawing Figures

GLC PROFILE FOR EXAMPLES I(A) & I(B) COMBINED 1st DISTILLATION PRODUCTS.

GLC PROFILE FOR EXAMPLE I(A). 1st DISTILLATION

GLC PROFILE FOR EXAMPLE II. DISTILLATION PRODUCT.

GLC PROFILE FOR EXAMPLES I(A) & I(B), BULKED FRACTIONS 6-13. 1ST REDISTILLATION

NMR SPECTRUM FOR FRACTION 13 OF EXAMPLES I(A) AND I(B) SECOND REDISTILLATION

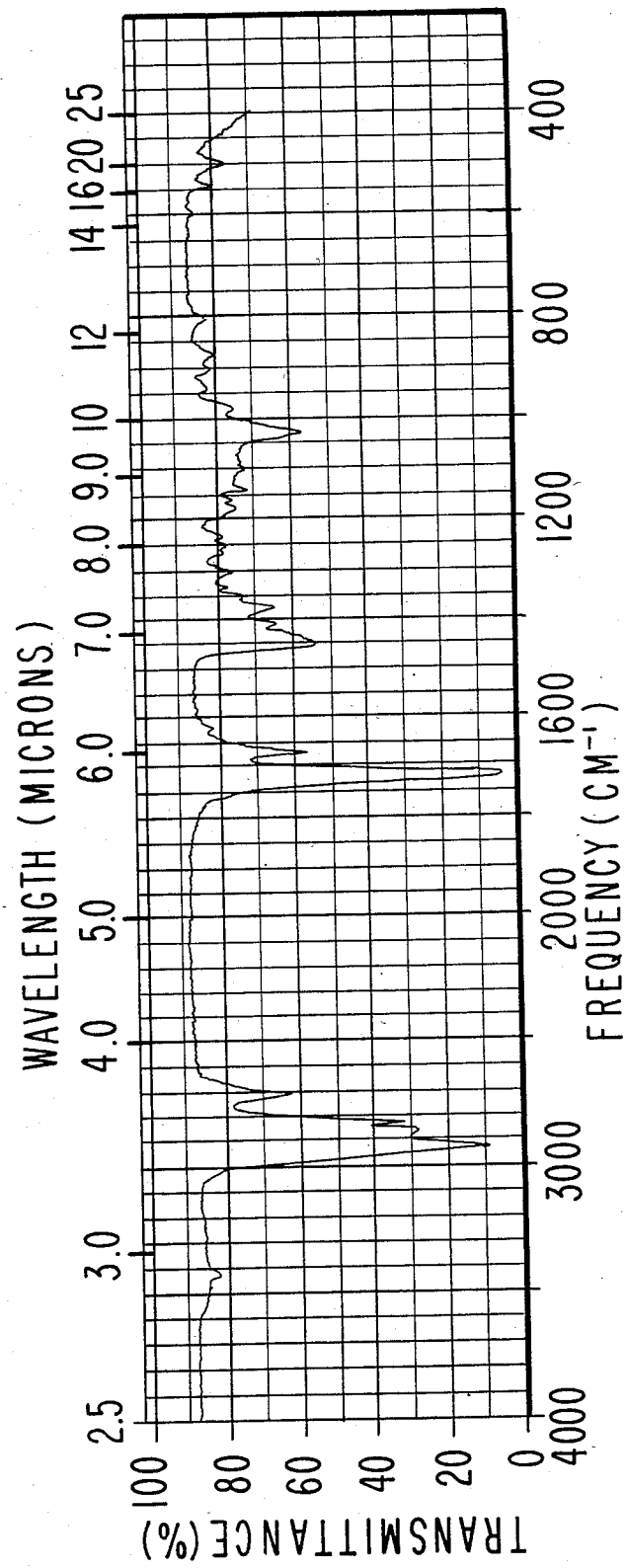

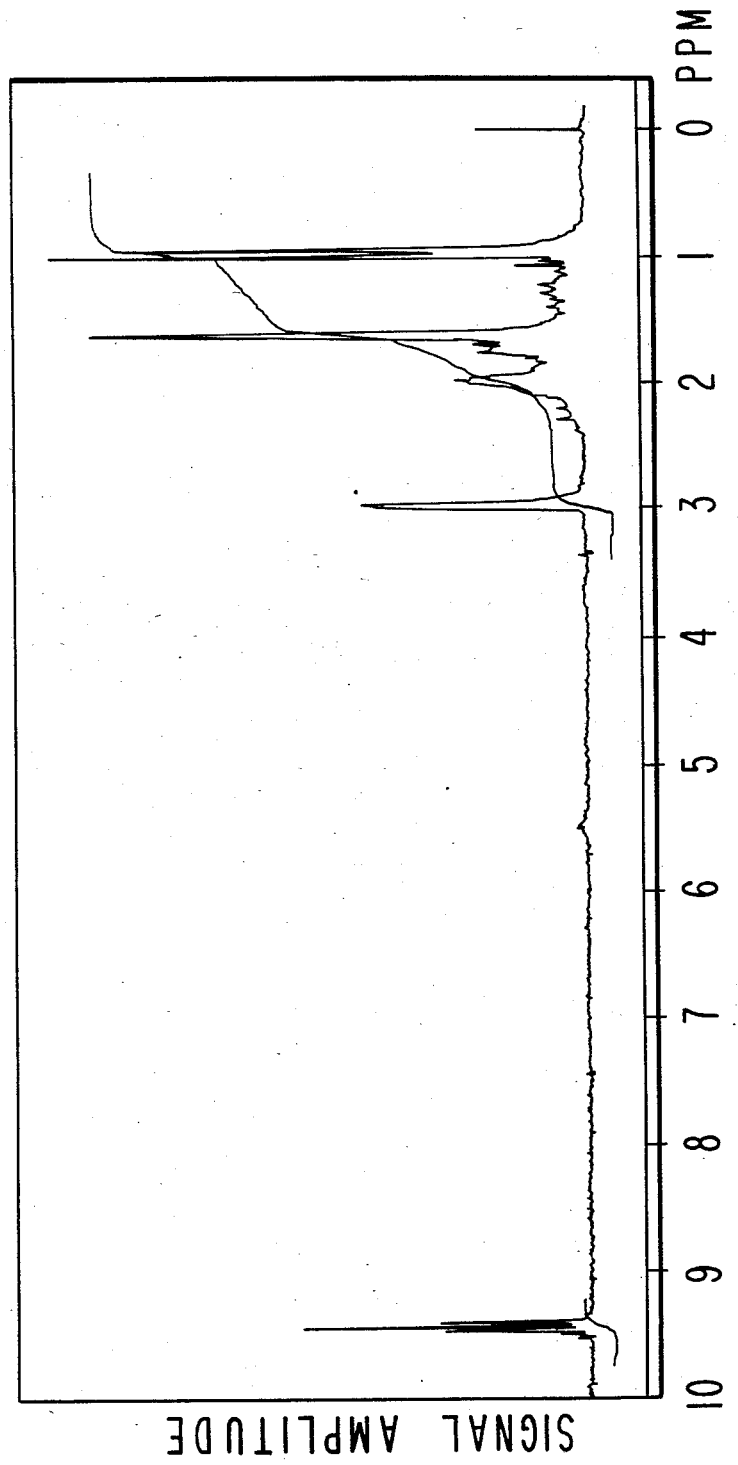

IR SPECTRUM FOR PEAK 64 OF FIG. 6, EXAMPLE II.

METHYL-SUBSTITUTED CYCLOHEXENYL ACETALDEHYDES, ORGANOLEPTIC USES THEREOF, PROCESSES FOR PRODUCING SAME AND INTERMEDIATES USEFUL THEREIN

BACKGROUND OF THE INVENTION

Our invention provides the genus of compounds described according to the structure:

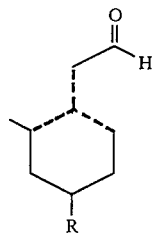

wherein R represents hydrogen or methyl and one of the dashed lines represents a carbon-carbon double bond and each of the other of the dashed lines represent carbon-carbon single bonds, mixtures of same, and organoleptic uses of a sub-genus of the foregoing compound which are methyl-substituted cyclohexenyl acetaldehydes defined according to the generic structure:

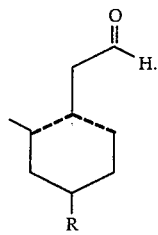

The methyl-substituted cyclohexenyl acetaldehydes having the structure:

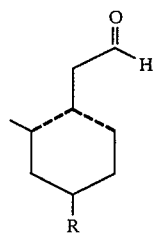

are useful in augmenting or enhancing the aroma or taste of consumable materials.

There has been considerable work performed relating to substances which can be used to impart, modify, alter or enhance fragrances to (or in) various consumable materials such as perfume compositions, colognes and perfumed articles such as soaps, colognes and detergents as well as perfumed polymers. These substances are used to diminish the use of natural materials, some of which may be in short supply and/or to provide more uniform properties in the finished product. Floral, fresh, green, vegetative tropical forest-like and piney aroma nuances are desirable in several types of perfume compositions, perfumed articles, colognes and perfumed polymers.

In addition, there has been considerable work performed relating to substances which can be used to impart, modify, alter or enhance flavors to (or in) various consumable materials such as foodstuffs, chewing gums, toothpastes and medicinal products. These substances are used to diminish the use of natural materials some of which may be in short supply and/or to provide more uniform properties in the finished product. Thus, strawberry, grape and raspberry flavored foodstuffs, chewing gums and medicinal products and toothpastes are highly desirable. Floral, fresh, green, parsley-like aroma and taste nuances are highly desirable in several types of flavor compositions.

U.S. Pat. No. 4,026,824 issued on May 31, 1977 discloses β-cyclohomocitral having the structure:

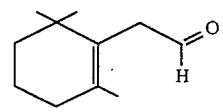

as useful in augmenting or enhancing the aromas of perfume compositions with respect to woody, camphoraceous, green, earthy and rosy nuances.

Arctander, "Perfume and Flavor Chemicals", 1969, at Volumes I and II discloses the use in perfume compositions and flavors of "cyclocitral", "isocyclocitral", "2,4-dimethyl butadieneacrolein", "3,4-dimethyl-Δ⁵-tetrahydrobenzaldehyde", "β-(4-methyl-3-cyclohexenyl)-butyraldehyde" and "tetrahydro-para-tolylaldehyde", thusly:

(i) "760 CYCLOCITRAL

α-cyclocitral=(2,2,6-trimethyl-5-cyclohexan-1-carboxaldehyde). β-cyclocitral=(2,2,6-trimethyl-6-cyclohexen-1-carboxaldehyde). Both isomers are known and have been produced separately.

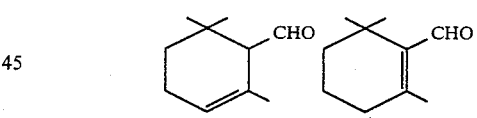

Very rarely offered commercially. These particular cyclocitrals have little or no interest to the creative perfumer, but they have served as part of many pieces of proof that isomers (α-β) do often have different odors."

(ii) "760:iso-CYCLOCITRAL

A mixture of two chemicals: 3,5,6-trimethyl-3-cyclohexen-1-carboxaldehyde (meta-cyclocitral).

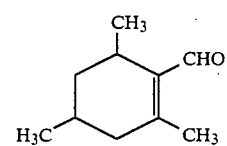

2,4,6-trimethyl-4-cyclohexen-1-carboxaldehyde (symmetric-iso-cyclocitral).

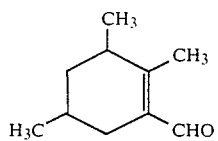

Powerful, and diffusive, foliage-green, "dark" weedy and dry odor, sometimes described as "Flower-shop odor". The earthy and wet-green notes are quite natural in high dilution and resemble the odor of stems from plants and flowers fresh from the soil.

Finds use in perfume compositions where it blends excellently with Oakmoss products (compensates from sweetness and lifts the topnote), with Inonoes (freshness), Geranium "vegetable" notes), etc . . . "

(iii) "996:2,4-DIMETHYL BUTADIENEACROLEIN

This material offered under the title name is:
2,4-Dimethyl tetrahydrobenzaldehyde
2,4-Dimethylcyclohex-3-enealdehyde.

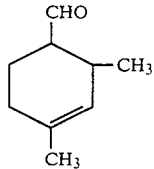

Colorless oily liquid.
Practically insoluble in water, soluble in alcohol and oils.
Moderately powerful, sweet-green, leafy odor of mediocre tenacity.

This aldehyde has, among several isomers and homologues, found some use in perfume compositions, mainly as part of new topnote compositions, specialties and bases.

It perfoms very well with Galbanum and Citrus oils, and it is compatible with floral, woody and herbaceous notes.

The material is rarely offered under its proper chemical name, although it was developed in an extensive research program by a large chemical company, not in the perfume chemical business, many years ago.

Interesting derivatives of potential use in perfume compositions have been prepared from this aldehyde (and its isomers and homologues) by condensation with Acetone, a process analogous to the Ionone synthesis. Many of the resulting Tetrahydrobenzylidene acetones are used in perfumes . . . "

(iv)
"1061:3,4-DIMETHYL-Δ⁵-TETRAHYDROBENZALDEHYDE 3,4-Dimethylcyclohex-5-enyl carboxaldehyde

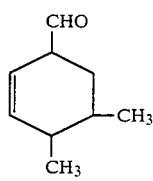

Colorless oily liquid.
Almost insoluble in water, soluble in alcohol and oils.
Powerful, green and rather dry-waxy, but in dilution very refreshing odor of moderate tenacity. It lacks natural character, but is rarely used as the "only aldehyde" component of any refreshing topnote or Aldehyde note.

The title aldehyde, related to Safranal (2,6,6-Trimethyl-) has found some use in perfume compositions as a powerful and refreshing ingredient with Citrus notes or woody notes. It is fairly stable in ordinary soap, and blends well with Cedarwood derivatives, Ionones, etc . . . "

(v)
"1974:β-(4-METHYL-3-CYCLOHEXENYL)-BUTYRALDEHYDE

I-Methyl-para-(3-Methylpropanal)-1-cyclohexene.
3-(4-Methyl-3-cyclohexenyl)-butanal.

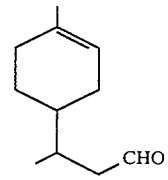

Colorless liquid.
Practically insoluble in water, soluble in alcohol and oils.

Sweet-floral odor with rosy-fruity undertones and moderate tenacity.

This material has—to the author's knowledge—not been offered commercially in practical amounts, but it was developed for use in perfumes, and its use was patented (patent recently expired).

It is probably still used as part or component of certain specialties and perfume bases, offered under trade name."

(vi)
"2928:TETRAHYDRO-para-TOLYLALDEHYDE

4-Methyl-3-cyclohexenedaldehyde.
4-Methyl-1,2,5,6-tetrahydrobenzaldehyde.

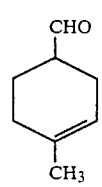

Colorless oily liquid. B.P. 169° C.
Practically insoluble in water, soluble in alcohol and oils.

Powerful, green-leafy odor, very diffusive and of poor tenacity.

The title aldehyde was developed in a program utilizing a new (at that time) method of synthesis for Cyclohexene aldehydes and their alkylsubstituted relatives.

It has been found a little use in perfume compositions, mainly in specialties for topnotes, and in bases, often accompanied by alifatic aldehydes, etc. and Citrus oils.

It has a sweeter character than the unsaturated C-6-aldehydes, but is not nearly as powerful or natural as those. As a supporting note in aldehydic bases, however, it has good effect, but it has not yet been offered commercially under its proper chemical name . . . "

β-Cyclocitral is disclosed as a volatile constituent of Greek Tobacco by Kimland, et al, Phytochemistry 11 (309) 1972. β-Cyclocitral is disclosed as a component of Burley Tobacco flavor by Demole and Berthet, Helv. Chim. Acta. 55 Fasc-6, 1866 (1972).

The reaction products and compounds of our invention however, which include those compounds defined according to the generic structure:

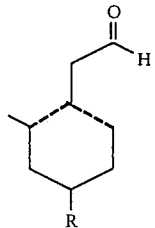

wherein one of the dashed lines represents a carbon-carbon double bond and the other of the dashed lines represents a carbon-carbon single bond and R represents hydrogen or methyl have unexpected, unobvious and advantageous organoleptic properties when compared with the compounds of the prior art.

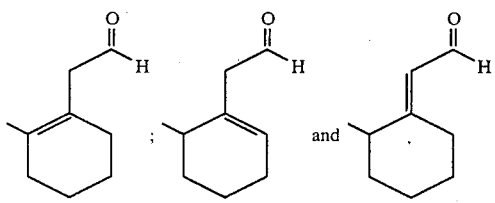

(Conditions: 20% SE-30 column, 15'×0.125" programmed at 150°-250° C. at 8° C. per minute).

Figure 2:
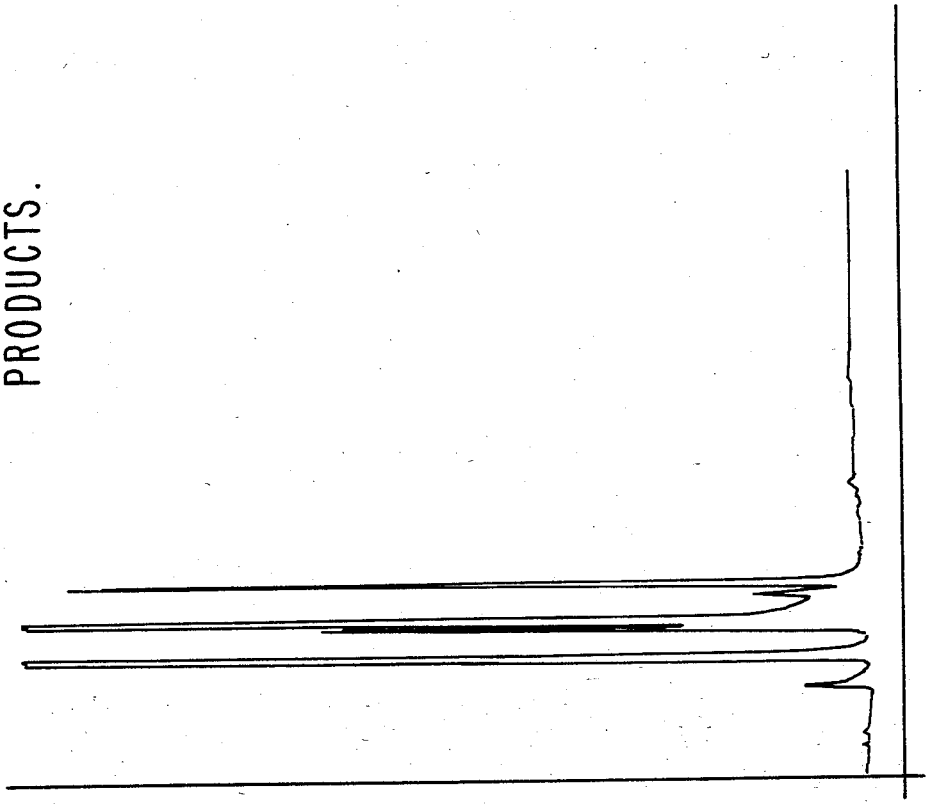

FIG. 2 is the GLC profile for the combined first distillation products of Examples I(A) and I(B) (Conditions: 20% SE-30 column, 15'×0.125" programmed at 150°-250° C. at 8° C. per minute).

Figures 3, 6:
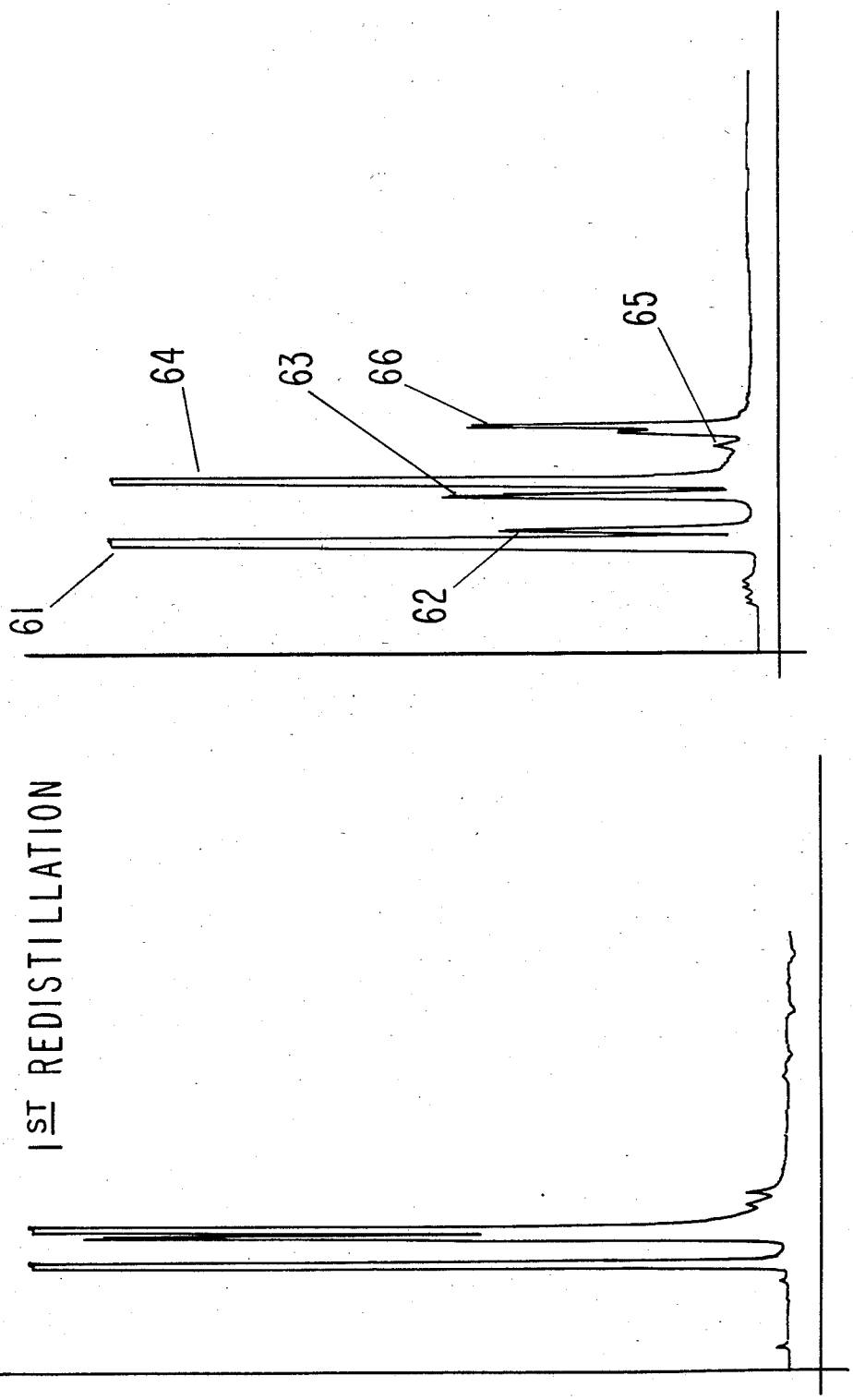

FIG. 3 is the GLC profile for the first redistillation product of combined Examples I(A) and I(B), bulked Fractions 6-13 (Conditions: 15'×0.125" 20% SE-30 column, programmed at 150°-250° C. at 8° C. per minute).

Figure 4:
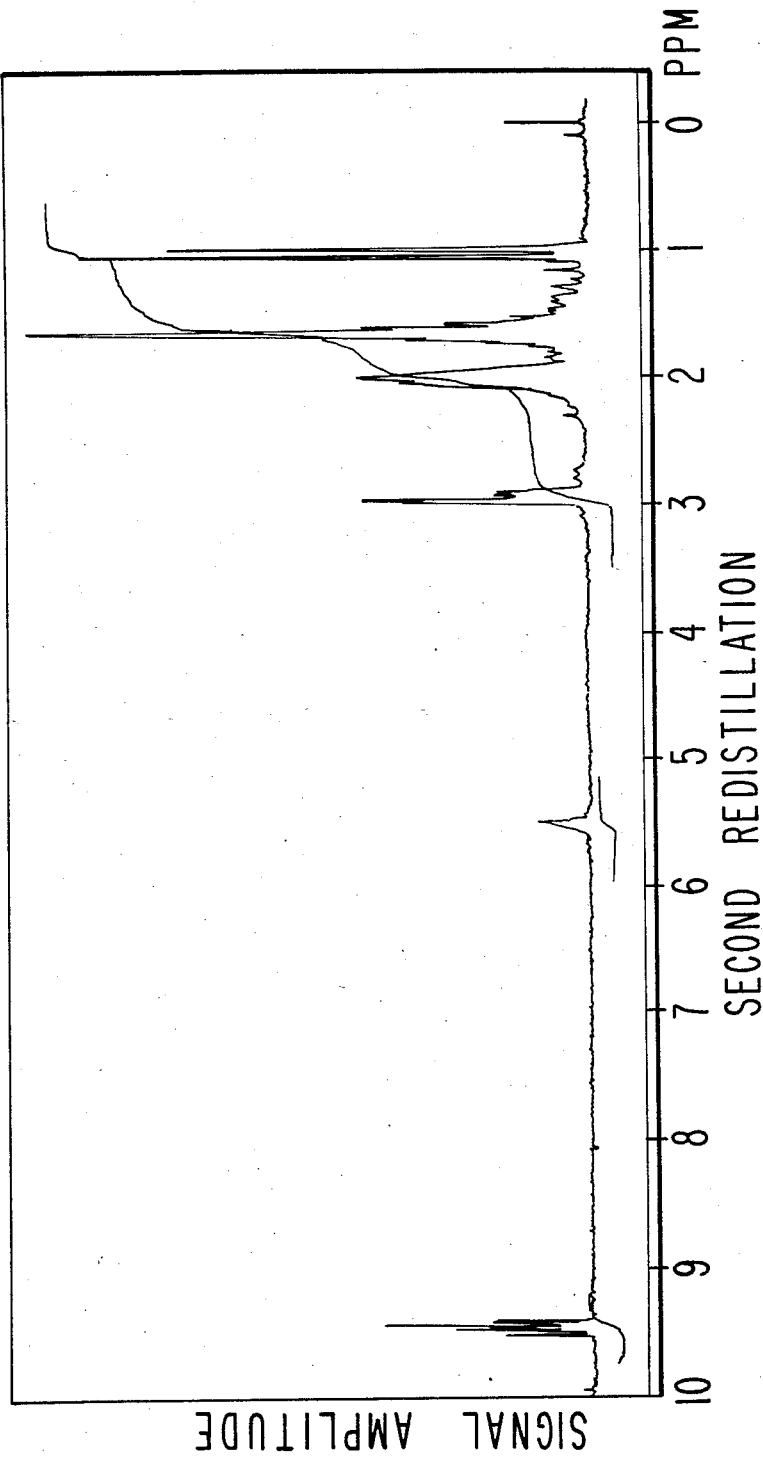

FIG. 4 is the NMR spectrum for the second distillation product of the reaction products of Examples I(A) and I(B), Fraction 13 containing the compounds having the structures:

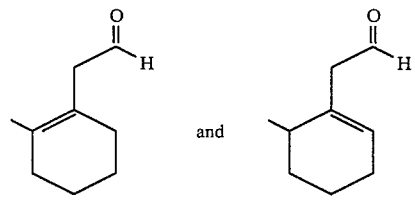

(Conditions: Field strength: 100 MHz; Solvent: CFCl₃).

FIG. 5 is the infra-red spectrum for the second redistillation product of the combined reaction products of Examples I(A) and I(B), Fraction 13 containing the compounds having the structures:

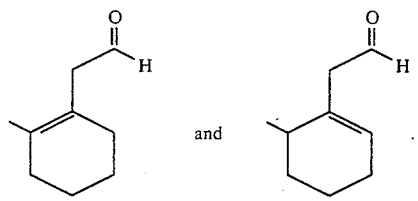

FIG. 6 is the GLC profile for the distillation product of the reaction product of Example II containing the compounds having the structures:

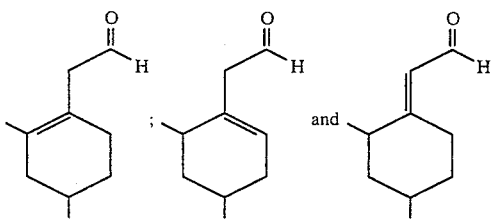

(Conditions: 15'×0.125" 20% SE-30 column, programmed at 150°-250° C. at 8° C. per minute).

FIG. 7 is the NMR spectrum for the peak indicated by reference numeral 64 on the GLC profile of FIG. 6 containing the compound having the structure:

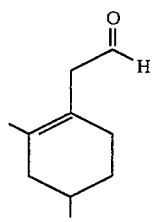

(Conditions: Field strength: 100 MHz; Solvent: CFCl₃).

Figure 8:
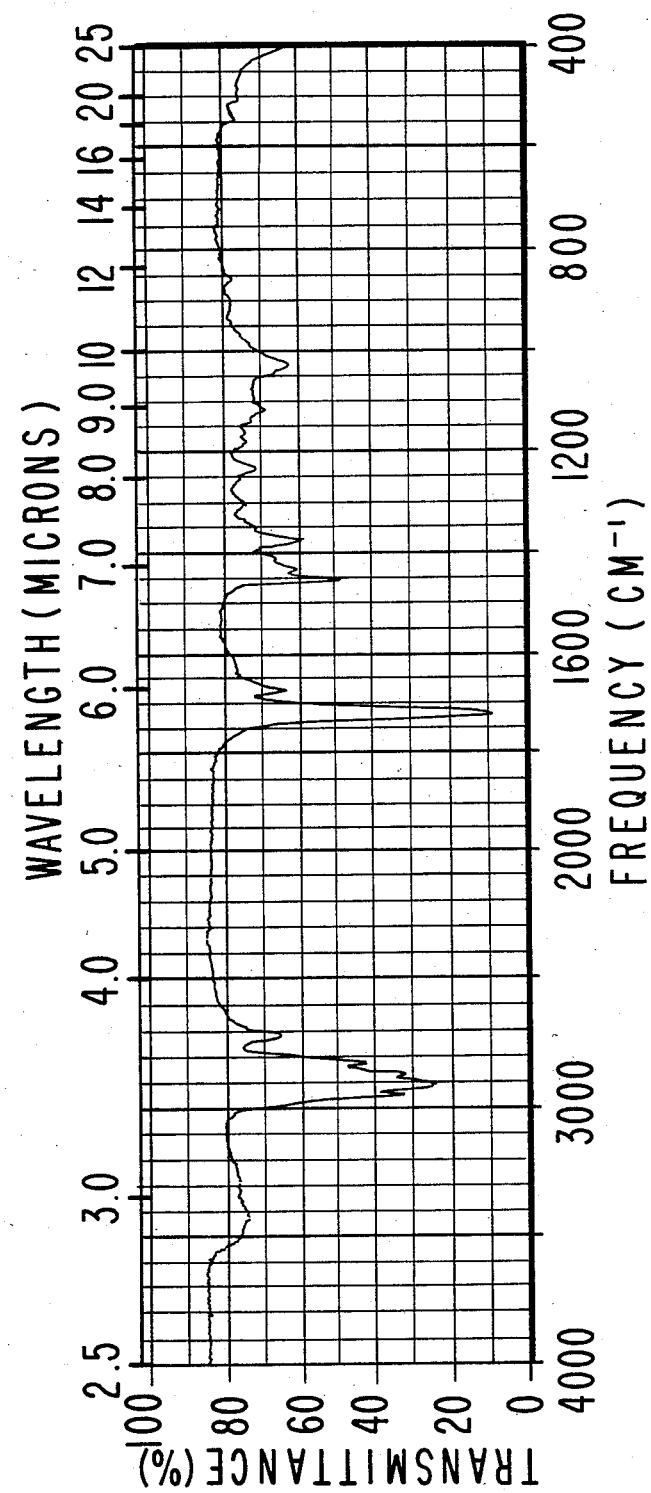

FIG. 8 is the infra-red spectrum for the peak indicated by reference numeral 64 on the GLC profile of FIG. 6 for the compound having the structure:

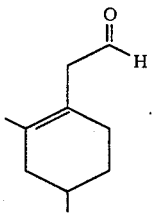

DETAILED DESCRIPTION OF THE DRAWINGS

Figure 1:
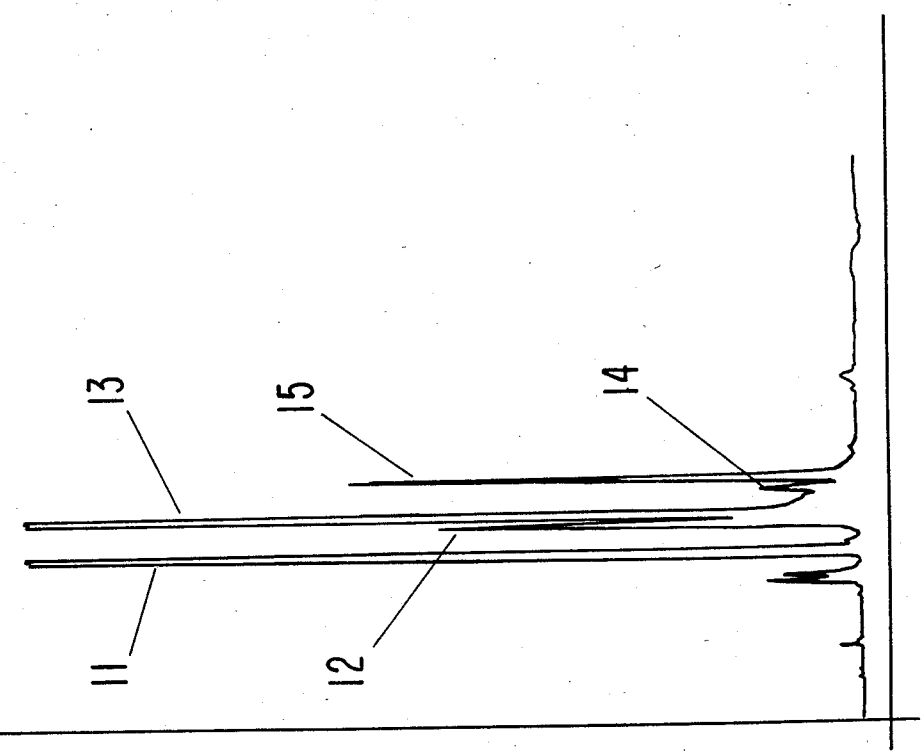
FIG. 1 is the GLC profile for the first distillation product of the reaction of Example I(A) containing the compounds having the structures.

Referring to FIG. 1, the GLC profile for the first distillation product of the reaction product of Example I(A) [Conditions: 15'×0.125" 20% SE-30 column, programmed at 150°-250° C. at 8° C. per minute], the peak indicated by reference numeral 11 is the peak for the starting material for the reaction having the structure:

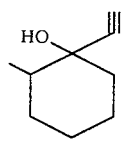

The peaks indicated by reference numerals 12 and 13 are the peaks for the compounds having the structures:

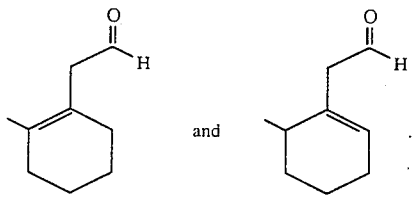

The peaks indicated by reference numerals 14 and 15 are the peaks for the intermediate conjugated aldehyde defined according to the structure:

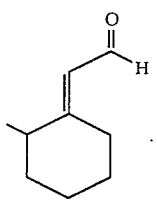

Referring to FIG. 6, the GLC profile for the distillation product of the reaction product of Example II (Conditions: 15'×0.125" 20% SE-30 column, programmed at 150°-250° C. at 8° C. per minute), the peaks indicated by reference numerals 61 and 62 are the peaks for the starting material defined according to the structure:

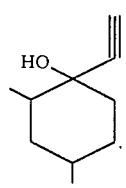

The peaks indicated by reference numerals 63 and 64 are the peaks for the products having the structures:

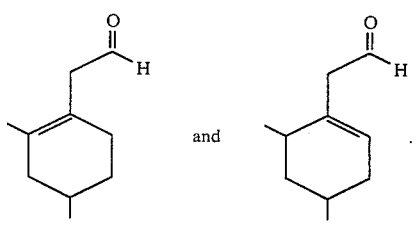

The peaks indicated by reference numerals 65 and 66 are the peaks for the intermediate reaction product defined according to the structure:

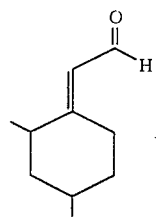

THE INVENTION

It has now been discovered that novel perfume compositions, colognes, perfumed articles and perfumed polymers having floral, fresh, green, vegetative tropical forest and piney aromas and novel foodstuffs, chewing gums, medicinal products and toothpastes having fresh, green, parsley-like aroma and taste nuances may be provided by utilization of compositions of matter containing one or mixtures of compounds defined according to the generic structure:

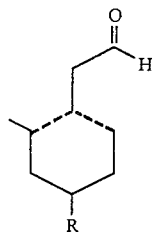

wherein R represents hydrogen or methyl and one of the dashed lines represents a carbon-carbon single bond and the other of the dashed lines represent a carbon-carbon double bond. Included in these mixtures may be the reaction intermediates defined according to the structures:

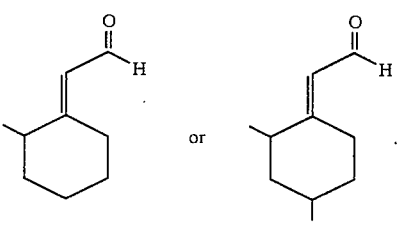

These compounds may be prepared by means of rearrangement of one of the "reactants" defined according to one of the structures:

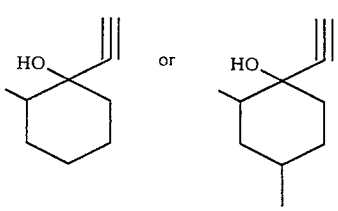

according to the reaction:

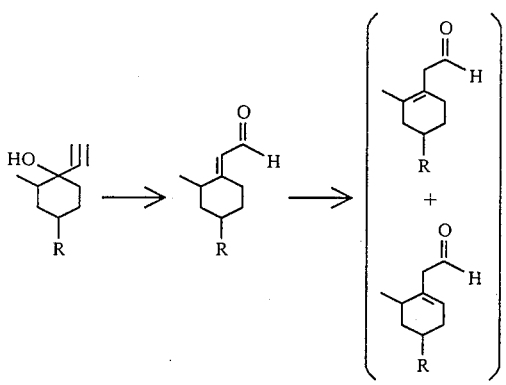

wherein R represents hydrogen or methyl using a tris(-triphenyl silyl)vanadate catalyst formed, in situ from triphenyl silanol having the structure:

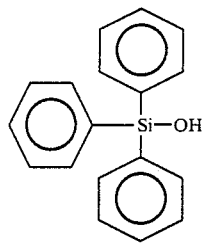

and vanadium triisopropoxide oxide or vanadium tri-n-propoxide oxide having the generic structure:

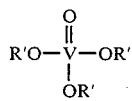

wherein R' represents n-propyl or isopropyl. The reaction is carried out at a temperature of between about 140° C. and 180° C. for a time period of from about 6 hours up to about 15 hours. The conditions of the reaction are substantially the same as those set forth in the article by Olson, et al in Helv. Chim. Acta. Volume 59, Fasc. 2 (1976) Nr. 59, at page 567 [title: "A Stereospecific Synthesis of Vitamin A from 2,2,6-Trimethylcyclohexanone"] the disclosure of which is incorporated by reference herein. At the end of the reaction, the reaction product is distilled from the reaction mass using a fractional distillation column, e.g., a multiplate vigreux column. Thus, for example, an 8 plate or a 12 plate vigreux column can be used. The catalyst is preferably prepared in mineral oil.

The resultant reaction product may then be further refined according to standard techniques, e.g., preparative gas chromatography and the like.

The methyl-substituted cyclohexenyl acetaldehydes of our invention are capable of supplying, modifying, altering or enhancing certain fragrance notes usually lacking in many perfumery materials, for example, petitgrain fragrances, floral fragrances and rose fragrances.

As used herein, the terms "alter" and "modify" in their various forms means "supplying or imparting fragrance character or notes to otherwise bland, relatively odorless substances or augmenting the existing aroma characteristic where aroma is deficient in some regard or supplementing the existing aroma impression to modify its quality, character or odor".

As used herein, the term "enhance" is intended to mean the intensification (without alteration "in kind") of an aroma note or nuance which is already existant in the organoleptic impression of a given perfume composition or perfumed article, cologne or perfumed polymer.

The methyl-substituted cyclohexenyl acetaldehydes and one or more auxiliary perfume ingredients, including for example, alcohols, aldehydes other than the methyl-substituted cyclohexenyl acetaldehydes of our invention, nitriles, esters, cyclic esters, and natural essential oils, may be admixed so that the combined odors of the individual components produce a pleasant and desired fragrance, particularly and preferably in floral fragrances, rosy fragrances, muguet fragrances or petitgrain fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute its particular olfactory characteristics, but the overall effect of the perfume composition will be the sum of the effects of each of the ingredients. Thus, the methyl-substituted cyclohexenyl acetaldehydes of our invention can be used to alter the aroma characteristics of a perfume composition, for example, by utilizing or moderating the olfactory reaction contributed by another ingredient in the composition.

The amount of methyl-substituted cyclohexenyl acetaldehydes of our invention which will be effective in perfume compositions depend on many factors, including the other ingredients, their amounts and the effects which are desired. It has been found that perfume compositions containing as little as 0.1% of the methyl-substituted cyclohexenyl acetaldehydes of our invention or even less (e.g., 0.05%) can be used to impart floral, fresh, green, vegetative tropical forest and piney aromas to soaps, cosmetics and other products. In addition, it has been found that such perfume compositions containing as little as 0.05% of the methyl-substituted cyclohexenyl acetaldehydes of our invention can be used to alter, modify or enhance floral, fresh, green, vegetative tropical forest and piney notes already present in soaps, cosmetics and other products. The amount employed can range up to 10% of the fragrance components and will depend on considerations of cost, nature of end product, the effect desired on the finished product and the particular fragrance sought.

The methyl-substituted cyclohexenyl acetaldehydes of our invention are useful, taken alone or in perfume compositions as an olfactory component in detergents and soaps, space odorants and deodorants, perfumes, colognes, toilet water, bath preparations, such as bath oils and bath solids; hair preparations such as lacquers, brilliantines, pomades and shampoos; cosmetic preparations such as creams, deodorants, hand lotions and sun screens; powders such as talcs, dusting powders, face powders and the like. As little as 0.5% of the methyl-substituted cyclohexenyl acetaldehydes will suffice to impart a floral, fresh, green, vegetative tropical forest or piney note to petitgrain formulations. As little as 4% of the methyl-substituted cyclohexenyl acetaldehydes of our invention will suffice to impart a tropical forest note in floral or muguet formulations. Generally, no more than 10% of the methyl-substituted cyclohexenyl acetaldehydes of our invention based on the ultimate end product is required in the perfume composition.

In addition, the perfume compositions or fragrance compositions of our invention can contain a vehicle or carrier for the methyl-substituted cyclohexenyl acetaldehydes of our invention. The vehicle can be a liquid such as a non-toxic alcohol (e.g., ethanol), a non-toxic glycol (e.g., propylene glycol) and/or a non-toxic ester (e.g., diethyl phthalate or the like). The carrier can also be an absorbent solid such as a gum (e.g., gum arabic, guar gum or xanthan gum) or components for encapsulating the gum (such as gelatin when encapsulation is carried out by means of coacervation or such as a urea-formaldehyde prepolymer when the encapsulation results in the formation of a ureaformaldehyde capsule wall around a liquid perfume center).

The methyl-substituted cyclohexenyl acetaldehydes of our invention defined according to the structure:

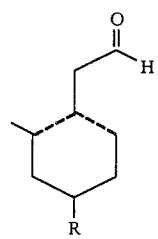

wherein one of the dashed lines represents a carbon-carbon double bond and the other of the dashed lines represents a carbon-carbon single bond and R represents hydrogen or methyl may be used as substantially pure compounds per se or may be formed in admixture as a result of the process which embodies the reaction:

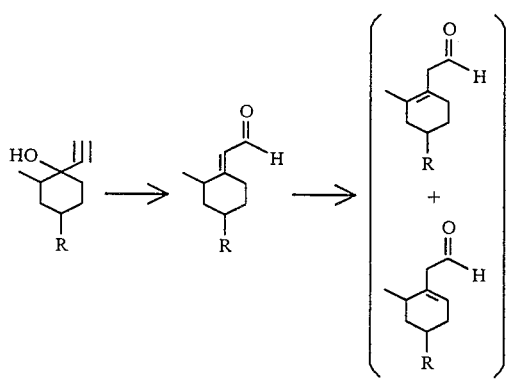

wherein R represents hydrogen or methyl. In such a reaction the resulting mixture not only contains the genus defined according to the structure:

but also contains the intermediates defined according to the structures:

and which intermediates do not detract from the organoleptic properties of the resultant composition. Indeed, a commercially viable form of product intended to be covered by the instant specification includes a reaction product formed by carrying out a rearrangement of the compound having the structure:

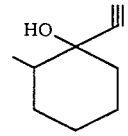

or the compound having the structure:

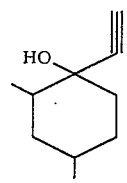

using the triphenyl silanol-vanadium trialkoxide oxide catalyst defined according to the structure:

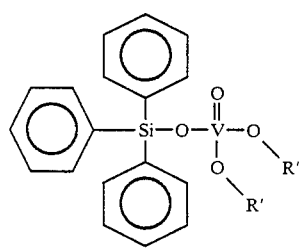

wherein R' represents n-propyl or isopropyl.

The genus of compounds defined according to the structure:

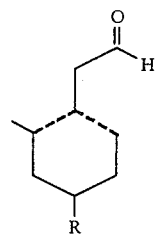

wherein one of the dashed lines represents a carbon-carbon double bond and the other of the dashed lines represents a carbon-carbon single bond and R represents hydrogen or methyl may be used to augment, alter, enhance or modify aroma or taste nuances in foodstuffs, chewing gums, medicinal products and toothpastes, particularly fresh, green, parsley-like nuances. Such a property causes an appropriate alteration of strawberry, grape and raspberry flavored foodstuffs, chewing gums, toothpastes and medicinal products.

The range of use of the methyl-substituted cyclohexenyl acetaldehydes of our invention in such foodstuffs, chewing gums, toothpastes and medicinal products is from about 0.1 ppm up to about 3 ppm. Adjuvants useful with the methyl-substituted cyclohexenyl acetaldehydes of our invention are as follows:

2-methyl-2-pentenic acid
2-methyl-3-pentenic acid
methyl and ethyl esters of 2-methyl-3-pentenic acid
methyl and ethyl esters of 2-methyl-2-pentenic acid
β-damascenone
α-damascenone
β-damascone
α-damascone
methyl anthranilate Examples I and II serve to illustrate the processes for production of the methyl-substituted cyclohexenyl acetaldehydes useful in our invention. Examples III, et seq. following serve to illustrate the utilities of the methyl-substituted cyclohexenyl acetaldehydes and products-by-processes claimed herein.

It will be understood that these Examples are illustrative and that the invention is to be considered restricted thereto only as indicated in the appended claims. All parts and percentages given herein are by weight unless otherwise specified.

EXAMPLE I

A. Production of 2 and 6-Methyl Cyclohexenyl Acetaldehyde

Reaction:

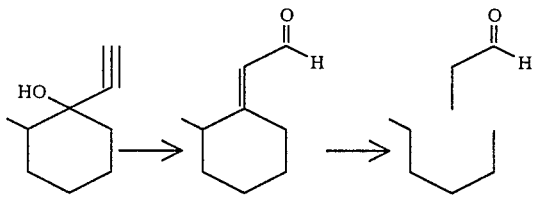

wherein a mixture is formed and in the mixture in each of the molecules one of the dashed lines is a carbon-carbon double bond and the other of the dashed lines is a carbon-carbon single bond.

Into a 300 cc three neck flask equipped with stirrer, thermometer, reflux condenser and heating mantle and previously flushed with nitrogen is placed 100 grams of PRIMOL ®, 6.46 grams of triphenyl silanol, 0.49 grams of vanadium triisopropoxide oxide having the structure:

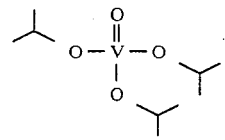

and 75 grams of the compound having the structure:

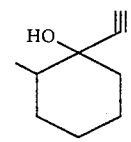

The reaction mass with stirring is heated to 140°–145° C. under a nitrogen blanket. The reaction mass is maintained at 140°–145° C. for a period of 12.5 hours.

At the end of the 12.5 hour period, the reaction product is distilled at a vapor temperature of 77°–82° C. at 20 mm/Hg. pressure.

FIG. 1 is the GLC profile of the distillation product (Conditions: 15'×0.125" 20% SE-30 column, programmed at 150°–250° C. at 8° C. per minute).

The peak indicated by reference numeral 11 is the peak for the starting material having the structure:

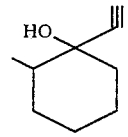

The peak indicated by reference numerals 12 and 13 are the peaks for the reaction products having the structures:

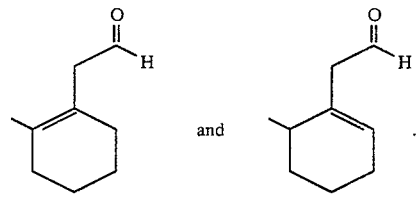

The peaks indicated by reference numerals 14 and 15 are the peaks for the intermediate having the structure:

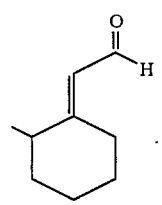

B. Preparation of 2(and 6) Methyl Cyclohexenyl Acetaldehyde

Reaction:

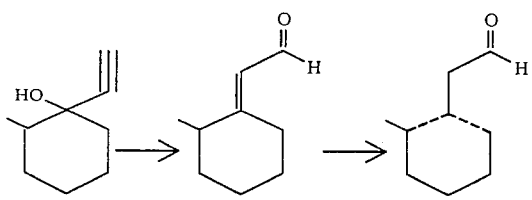

(wherein a mixture is formed and in the mixture in each of the molecules one of the dashed lines is a carbon-carbon double bond and the other of the dashed lines is a carbon-carbon single bond).

Into a 250 cc flask equipped with stirrer, thermometer, reflux condenser, heating mantle and nitrogen blanket apparatus is placed 100 grams PRIMOL®, 6.46 grams triphenyl silanol, 0.49 grams of vanadium tri-n-propoxide oxide having the structure:

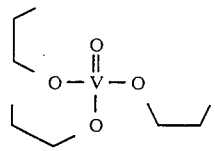

and 75 grams of the compound having the structure:

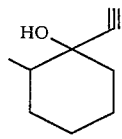

The reaction mass, with stirring, is heated to a temperature in the range of 145°-158° C. and maintained at that temperature range for a period of eleven hours. At the end of the eleven hour period, the reaction mass is distilled at a vapor temperature of 77°-85° C. at 20 mm/Hg. pressure.

The resulting distillation product is combined with the distillation product of Example I(A).

FIG. 2 is the GLC profile for the combined distillation products (Conditions: 15'×0.125" 20% SE-30 column, programmed at 150°-250° C. at 8° C. per minute).

The resulting product is then distilled on an 8 plate vigreux column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 77 | 89 | 20 | 9.29 |
| 2 | 70 | 89 | 20 | 10.88 |
| 3 | 77 | 88 | 20 | 8.90 |
| 4 | 77 | 89 | 20 | 9.92 |
| 5 | 77 | 90 | 20 | 10.73 |
| 6 | 78 | 92 | 18 | 10.49 |
| 7 | 79 | 94 | 20 | 11.30 |
| 8 | 80 | 114 | 20 | 8.95 |
| 9 | 80 | 118 | 20 | 9.43 |
| 10 | 81 | 121 | 20 | 9.88 |
| 11 | 82 | 122 | 20 | 10.22 |
| 12 | 82 | 125 | 20 | 11.57 |
| 13 | 85 | 119 | 12 | 3.46 |
| 14 | 90 | 142 | 12 | 4.09 |
| 15 | — | 165 | 55 | 3.07 |

FIG. 3 is the GLC profile for bulked Fractions 6-13 (Conditions: 15'×0.125" 20% SE-30 column programmed at 150°-250° C. at 8° C. per minute).

Bulked Fractions 6-13 are redistilled on a 12 plate vigreux column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 92 | 98 | 50 | 3.42 |
| 2 | 82 | 88 | 27 | 3.13 |
| 3 | 84 | 88 | 27 | 5.68 |
| 4 | 84 | 88 | 27 | 5.14 |
| 5 | 85 | 89 | 27 | 8.24 |
| 6 | 86 | 92 | — | 10.62 |
| 7 | 85 | 93 | 27 | 5.38 |
| 8 | 85 | 95 | 27 | 6.07 |
| 9 | 87 | 105 | 28 | 6.67 |
| 10 | 87 | 113 | 28 | 7.83 |
| 11 | 85 | 185 | 28 | 3.61 |
| 12 | 72 | 180 | 10 | 2.55 |

Fractions 6-11 and 13 are combined and are evaluated as containing the compounds having the structures:

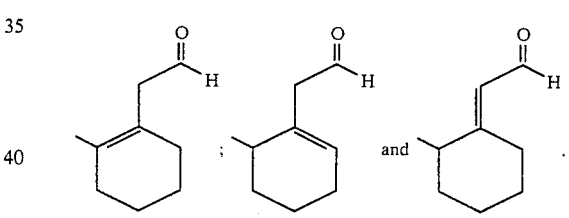

The resulting product has a floral, fresh, green, vegetative tropical forest aroma from a perfume standpoint and has a green parsley-like aroma and taste profile from a flavor standpoint causing it to be useful in strawberry, grape and raspberry flavored foodstuffs, chewing gums, medicinal products and toothpastes.

FIG. 4 is the NMR spectrum for Fraction 13 of the foregoing distillation on the 12 plate vigreux column (Conditions: Field strength: 100 MHz; Solvent: CFCl₃).

Fraction 13 contains only the compounds having the structures:

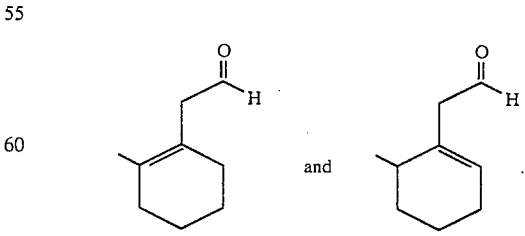

FIG. 5 is the infra-red spectrum for Fraction 13 of the foregoing second distillation carried out on the 12 plate vigreux column. Fraction 13 only contains the compounds having the structures:

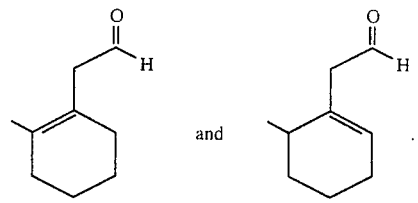

and

EXAMPLE II

PREPARATION OF 2,4 AND 4,6-DIMETHYLCYCLOHEXENYL

Reaction:

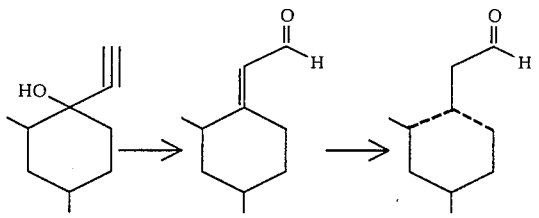

wherein a mixture is formed and in the mixture, in each of the molecules one of the dashed lines is a carbon-carbon double bond and the other of the dashed lines is a carbon-carbon single bond.

Into a three neck 250 cc reaction vessel equipped with stirrer, thermometer, reflux condenser and heating mantle are placed the following materials;

| | |
|---|---|
| PRIMOL ® | 100.0 grams |
| Triphenyl silanol having the structure: | 6.5 grams |
| Vanadium triisopropoxide oxide having the structure: | 0.5 grams |
| Benzoic acid | 150.0 micrograms |
| The compound having the structure: | 100.0 grams |

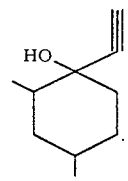

The resulting mixture with stirring is heated to 140°-145° C. under a nitrogen blanket. The reaction mass is heated at 140°-145° C. for a period of 14 hours. The resulting reaction product is then distilled on a short path column at 2.5 mm/Hg. at a vapor temperature of 76° C. and a pot temperature of 146° C.

The resulting product, weighing 49.5 grams is then evaluated for its aroma properties. It has a green aesthetically pleasing, intense and long-lasting piney, green aroma and a fresh parsley green aroma and taste profile for foodstuffs, chewing gums, toothpastes and medicinal products.

FIG. 6 is the GLC profile for the resulting distillation product (Conditions: 15'×0.125" SE-30 column programmed at 150°-250° C. at 8° C. per minute).

The peaks indicated by reference numerals 61 and 62 are the peaks for the starting material having the structure:

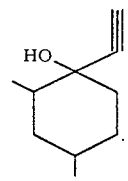

The peaks indicated by reference numerals 63 and 64 are the peaks for the reaction product having the structures:

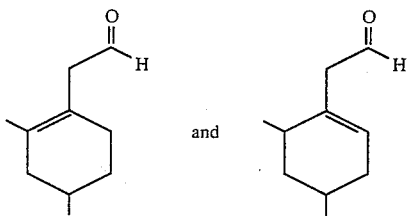

and

The peaks indicated by reference numerals 65 and 66 are for the intermediate compound having the structure:

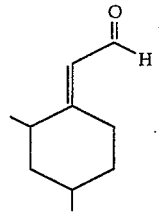

FIG. 7 is the NMR spectrum for the peak indicated by reference numeral 64 on FIG. 6, the GLC profile for the compound having the structure:

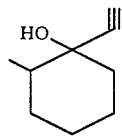

(Conditions: Field strength: 100 MHz; Solvent: CFCl$_3$).

FIG. 8 is the infra-red spectrum for the peak indicated by reference numeral 64 on the GLC profile of FIG. 6, for the compound having the structure:

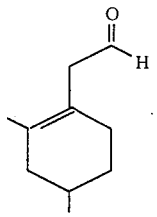

EXAMPLE III

MUGUET PERFUME FORMULATION

The following formulation is prepared:

| Ingredients | Parts by Weight |
|---|---|
| Indole | 2 |
| Hexyl Cinnamic Aldehyde | 400 |
| Rhodinol | 40 |
| Terpineol | 30 |
| Tetrahydro-3-pentyl-pyran-4-ylacetate | 10 |
| Cinnamyl Acetate | 5 |
| 4 (4-hydroxy-4-methylpentyl)-3-cyclo-hexene-l-carboxaldehyde | 20 |
| Hydroxy Citronellal | 280 |
| Violet Leaves Absolute (10% in diethyl phthalate) | 4 |
| Phenyl ethyl alcohol | 45 |
| Tetrahydromuguol | 20 |
| n-Undecylenic Aldehyde (20% in diethyl phthalate) | 5 |
| n-decanal (10% in diethyl phthalate) | 5 |
| n-nonanal (10% in diethyl phthalate) | 4 |
| Benzyl acetate | 10 |
| Dimethyl Phenyl Ethyl Carbinol | 10 |
| p-t-butyl-alpha-methyl-hydrocinnamic aldehyde | 4 |
| Methyl Cinnamate (10% in diethyl phthalate) | 2 |
| Benzyl Cinnamate | 4 |
| | 940 |

40 Parts by weight of a mixture of compounds having the structures:

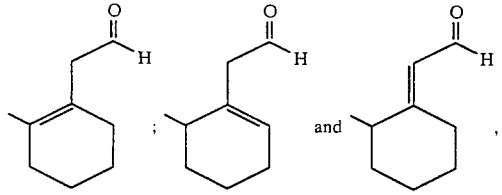

bulked Fractions 6-11 and 13 of the distillation of the reaction products of Examples I(A) and I(B) is added to the above formulation. This reaction product improves the floral nuance of the formulation by adding a floral, fresh, green vegetative tropical forest undertone to the formulation. The resulting perfume formulation is thus described as "a muguet aroma with floral, fresh, green, vegetative tropical forest undertones".

EXAMPLE IV

FLORAL PERFUME FORMULATION

The following floral formulation is prepared:

| Ingredients | Parts by Weight |
|---|---|
| Lavendar Barreme | 60 |
| Linalool | 370 |
| Phenyl Ethyl Alcohol | 500 |
| Benzyl acetate | 120 |
| Linalyl Acetate | 520 |
| Hydroxy Citronellal | 600 |
| 4 (4-hydroxy-4-methylpentyl)-3-cyclohexene-1-carboxaldehyde | 100 |
| Eugenol | 230 |
| Alpha isomethyl ionone | 1000 |
| Sandalwood Oil | 120 |
| Ylang Oil | 50 |
| Musk Ambrette | 100 |
| Benzyl Salicylate | 1350 |
| 6-oxa-1,1,2,3,3,8-hexamethyl-1-2,3,5,6,7,8-hexahydro-1H-Benze[f]-indene prepared according to the process of Example XV of U.S. Pat. No. 3,360,530 (50% in diethyl phthalate) | 550 |
| 4'-t-butyl-2',6'-dimethyl-3',5'-dinitro acetophenone | 450 |
| p-t-butyl-alpha-methyl-hydrocinnamic aldehyde | 20 |
| diethyl phthalate | 90 |
| | 6230 |

35 Parts by weight of the mixture of compounds having the structures:

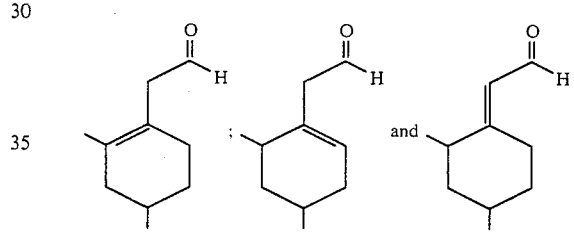

prepared according to Example II (distillation at 2.5 mm/Hg. pressure, 76° C. vapor temperature) is added to the resulting formulation. The mixture of compounds having the structures:

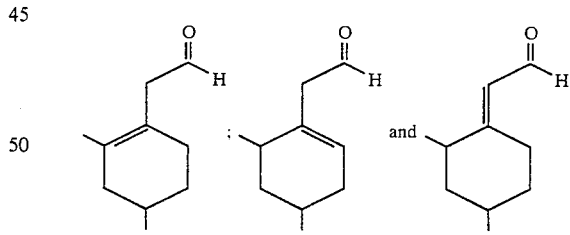

imparts to this floral fragrance an intense piney green undertone. Accordingly, the foregoing perfume formulation can be described as "floral with piney and green undertones".

EXAMPLE V

PREPARATION OF A COSMETIC POWDER COMPOSITION

A cosmetic powder is prepared by mixing in a ball mill 100 grams of talcum powder with 0.25 grams of one of the substances set forth in Table I, supra. The resulting powders have excellent aromas as set forth in Table I, supra:

TABLE I

| Perfume Substance | Aroma Description |
| --- | --- |
| Perfume composition of Example III. | A muguet aroma with floral, fresh, green, vegetative tropical forest undertones. |
| Perfume composition of Example IV. | A floral with piney and green undertones. |
| The mixture of compounds having the structures: 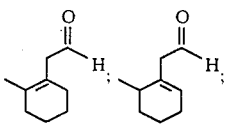 bulked distillation Fractions 6-11 and 13 produced according to Examples I(A) and I(B). | A floral, fresh, green and vegetative tropical forest aroma profile. |
| The mixture of compounds having the structures: 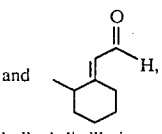 produced according to Example II distilling at 2.5 mm/Hg. pressure at 76° C. vapor temperature. | A piney, green aroma profile. |

EXAMPLE VI

PERFUMED LIQUID DETERGENT

Concentrated liquid detergents (Lysine salt of n-dodecylbenzene sulfonic acid as more specifically described in U.S. Pat. No. 3,948,818 issued on Apr. 6, 1976 the specification for which is incorporated herein) with aromas as set forth in Table I of Example V, supra, are prepared containing 0.10%, 0.15%, 0.20%, 0.30% and 0.40% of the substances set forth in Table I of Example V. They are prepared by adding and homogeneously mixing the appropriate quantity of perfume substance set forth in Table I of Example V in the liquid detergents.

The detergents all possess excellent aromas, the intensity increasing with greater concentration of perfume substance set forth in Table I of Example V.

EXAMPLE VII

PREPARATION OF A SOAP COMPOSITION

One hundred grams of soap chips prepared by chopping up a soap prepared as follows according to Japanese Pat. No. 79/28846 assigned to Kawaken Fine Chemicals Company:

"Fatty acid monoisopropanolamide ethoxylate 30 pts. and $P_2O_3$ 2.5 pts. are reacted and the product is combined with triethanolamine phosphate in a basic soap material and made into soap cakes"

are admixed with one gram (separately) of each of the substances of Table I of Example V until homogeneous compositions are obtained. In each of the cases, the homogeneous compositions are heated under three atmospheres pressure at 180° C. for a period of three hours and the resulting liquids are placed into soap molds. The resulting soap cakes, on cooling, manifest excellent aromas as set forth in Table I of Example V.

EXAMPLE VIII

PREPARATION OF A SOLID DETERGENT COMPOSITION

A detergent is prepared from the following ingredients according to Example I of Canadian Pat. No. 1,007,948 the specification for which is incorporated by reference herein:

| Ingredients | Parts by Weight |
| --- | --- |
| "Neodol 45-11" (a $C_{14}$—$C_{15}$ alcohol ethoxylated with 11 moles of ethylene oxide) | 12 |
| Sodium carbonate | 55 |
| Sodium citrate | 20 |
| Sodium Sulfate, water brighteners | q.s. |

This detergent is a "phosphate-free" detergent. A total of 100 grams of this detergent is admixed with 0.15 grams (separately) of each of the perfume substances of Table I of Example V, supra. Each of the detergent samples have excellent aromas as set forth in Table I of Example V.

EXAMPLE IX

PREPARATION OF A COLOGNE AND HANDKERCHIEF PERFUME

Each of the perfume substances as set forth in Table I of Example V is incorporated into a cologne at concentrations of 2.0%, 2.5%, 3.0%, 3.5%, 4.0%, 4.5% and 5.0% in 80%, 85%, 90% and 95% aqueous food grade ethanol; and into handkerchief perfumes at concentrations of 15%, 20%, 25% and 30% (in 90% and 95% aqueous food grade ethanol solutions). Distinct and definite aromas which are aesthetically pleasing as set forth in Table I of Example V are imparted to each of the colognes and to each of the handkerchief perfumes at all levels as indicated above.

EXAMPLE X

Utilizing the procedure of Example I at column 15 of U.S. Pat. No. 3,632,396 the specification for which is incorporated by reference herein, a nonwoven cloth substrate useful as a dryer-added fabric-softening article of manufacture is prepared wherein the substrate, the substrate coating and the outer coating and the perfuming material are as follows:
1. A water "dissolvable" paper ("Dissolvo Paper");
2. Adogen 448 (m.p. about 140° F.) as the substrate coating; and
3. An outer coating having the following formulation:
   57 percent $C_{20-22}$ HAPS
   22 percent isopropyl alcohol
   20 percent antistatic agent 1 percent (separately) of each of the perfume substances set forth in Table I of Example V giving rise to the aroma nuances as set forth in Table I of Example V.

Fabric-softening compositions are prepared as set forth above having the aroma characteristics as set forth in Table I of Example V essentially consist of a substrate having a weight of about 3 grams per 100 square inches; a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate.

The aroma as set forth in Table I of Example V are imparted in a pleasant manner to the head space in the dryer on operation thereof using the said dryer added fabric softening nonwoven fabric.

EXAMPLE XI

RASPBERRY FLAVORED BEVERAGE

A raspberry syrup is prepared by first formulating the following raspberry flavor:

| Ingredients | Parts by Weight |
| --- | --- |
| Natural raspberry extract | 40.0 |
| Beta-homocyclocitral | 14.0 |
| 4(4-Hydroxy-4-methylphenyl)-3-cyclo-hexene-1-carboxyaldehyde | 20.0 |
| Trans-trans-Δ-damascone | 14.0 |
| β-Damascone | 4.0 |
| β-Damascenone | 8.0 |
| The mixture of compounds having the structures: 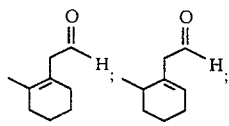 prepared according to Example I, bulked distillation Fractions 6-11 and 13. | 8.0 |

At the rate of 0.5 percent the resulting flavor formulation is added to a sugar syrup. The resulting syrup is admixed at the level of 10 percent with carbonated water. The resulting beverage has an excellent natural raspberry aroma with a raspberry "seed" character which is not present when the product produced according to Example I is not added. The raspberry kernel character is further enhanced by adding at the rate of 3 percent, the mixture of compounds having the structures:

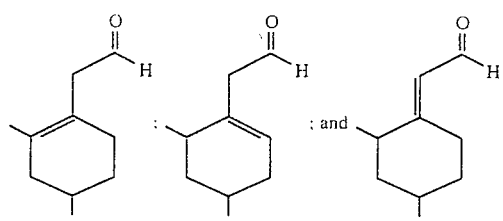

produced according to Example II to the flavor formulation.

The above-mentioned raspberry flavor is also added to chewing gum at the rates of 5 ppm, 10 ppm, 15 ppm, 30 ppm, 50 ppm and 100 ppm. In all cases chewing gums have excellent raspberry flavors which are long-lasting.

What is claimed is:

1. A process for augmenting or enhancing the aroma or taste of a consumable material selected from the group consisting of perfume compositions, colognes, perfumed articles, perfumed polymers, foodstuffs, chewing gums, medicinal products and toothpastes comprising the step of adding to said consumable material a product consisting essentially of a mixture of compounds having the structures:

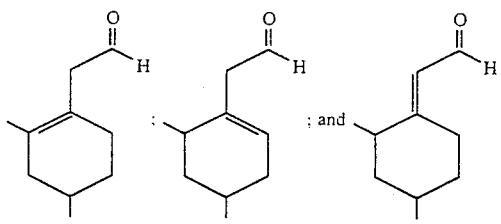

prepared according to the process of reacting the compound having the structure:

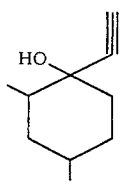

in the presence of a catalyst consisting essentially of triphenyl silanol having the structure:

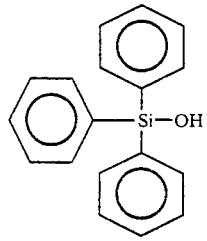

and a vanadium trialkoxy oxide having the structure:

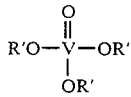

wherein R' represents n-propyl or isopropyl.

2. The process of claim 1 wherein the consumable material is a perfume composition, cologne or perfumed polymer.

3. The process of claim 1 wherein the consumable material is a foodstuff or chewing gum.

* * * * *